United States Patent [19]
Park et al.

[11] Patent Number: 6,152,869
[45] Date of Patent: Nov. 28, 2000

[54] RADIOACTIVE STENT AND PROCESS FOR PREPARATION THEREOF

[75] Inventors: Kyung Bae Park, Taejon-si; Jong Doo Lee, Seoul, both of Rep. of Korea

[73] Assignee: Korea Atomic Research Energy Research Institute, Taejon-si, Rep. of Korea

[21] Appl. No.: 09/132,161

[22] Filed: Aug. 10, 1998

[30] Foreign Application Priority Data

Dec. 24, 1997 [KR] Rep. of Korea ................. 97-73440

[51] Int. Cl.[7] ............................................ A61N 5/00
[52] U.S. Cl. ......................................................... 600/3
[58] Field of Search ............................ 600/1–8; 606/108, 606/192, 194, 198

[56] References Cited

U.S. PATENT DOCUMENTS

| | | |
|---|---|---|
| 4,739,762 | 4/1988 | Palmaz . |
| 4,776,337 | 10/1988 | Palmaz . |
| 5,064,435 | 11/1991 | Porter . |
| 5,176,617 | 1/1993 | Fischell et al. ............................. 600/3 |
| 5,213,561 | 5/1993 | Weinstein et al. . |
| 5,282,824 | 2/1994 | Gianturco . |
| 5,354,257 | 10/1994 | Roubin et al. . |
| 5,370,691 | 12/1994 | Samson . |
| 5,722,984 | 3/1998 | Fischell et al. ............................. 600/3 |

FOREIGN PATENT DOCUMENTS

96/10436 4/1996 WIPO .

*Primary Examiner*—John P. Lacyk
*Attorney, Agent, or Firm*—Dilworth & Barrese

[57] ABSTRACT

The present invention relates to a radioactive stent surrounded with a flexible sleeve containing radionuclides and processes for preparation thereof, which can be used to treat arteriosclerosis, hepatobiliary duct cancer and esophageal cancer efficiently since the stent prevents the restenosis of coronary artery and the penetration of cancer cells into lumen.

8 Claims, 8 Drawing Sheets

RADIOACTIVE STENT AND PROCESS FOR PREPARATION THEREOF

FIELD OF THE INVENTION

The present invention relates to a radioactive stent surrounded with a flexible sleeve containing radionuclides and process for preparation thereof, which can be used for preventing restenosis of coronary artery and penetration of cancer cells into lumen, in esophageal cancer and hepatobiliary duct cancer.

BACKGROUND OF THE INVENTION

Percutaneous transluminal coronary angioplasty has been operated to treat coronary-stenosing diseases such as arteriosclerosis and the like. The angioplasty was first performed in human body by Gruenzig et al. in 1977 and it has been firmly established as a curative method for treating coronary diseases. Presently, 500,000 people per year have been reported to be treated with the method worldwidely (Holmes, D. R. et al., Am. J. Cardiol., 53: 77C–81C, 1984). In Korea, the angioplasty has also been performed actively, especially at the university hospitals.

Since operational apparatuses for the percutaneous transluminal coronary angioplasty were developed diversely, the angioplasty has been widely performed so as to be applied to various diseases. Practically, the angioplasty has been operated in single vessel disease and multiple vessel disease, stable angina pectoris and instable angina pectoris, acute myocardial infarction and the like (Nobuyoshi, M. et al., J. Am. Coll. Cardiol., 17: 198B, 1991; Waller, B. F. et al., J. Am. Coll. Cardiol., 17: 58B–70B, 1991).

Although the angioplasty treated by using the balloon dilatation catheter, etc. succeeded clinically at the rate of 95%, acute closure and restenosis can be induced before and after the operations.

The restenosis described above may be induced by the mechanisms such as the vascular remodeling, the abnormal proliferation of the injured smooth muscle cell (SMC), the formation of extracellular matrix and the like (Wither, H. R. et al., Cancer, 34: 39–47, 1974; Thames, H. D. et al., Int. J. Radiat. Onco. Biol. Phys., 7: 1591–1597, 1981).

Although the smooth muscle cell within the vessel is not proliferative normally, physical defects and stimuli incite smooth muscle cell to migrate into the inner layer of blood vessel, to multiply or to form a matrix tissue.

In the early days of coronary angioplasty, such a restenosis would occur in approximately 30–45% of treated patients. New methods such as atherectomy, rotabulation, use of transluminal extraction catheter (TEC), excimer laser coronary angioplasty and inserting stents made of metallic wire (1) as shown in FIG. 1 have been accomplished in order to reduce the restenosis rate.

The above methods were also performed by using antithrombocyte agent, anti-coagulant, steroids, calcium channel blocker, colchicine and the like coincidently in order to prevent the restenosis. But effective drugs reducing the restenosis has not been discovered yet. Recently, local drug delivery and gene therapy are prevailing and they show good effects in in vitro study, but the effects shown in in vivo study are not certain. The uncertainty of effects of such treatment results from the blood flow washing off the above drugs in the blood vessel. Therefore it is difficult to administer the drugs in the blood vessel and especially in specific sites of the vessel.

However, no operation has been reported to reduce the induction rate of the restenosis outstandingly except the insertion of stents which expands and supports the restenosed sites.

Regarding the treatment of esophageal cancer, the esophagus site which is stenosed due to cancer cell proliferation should be enlarged physically to enable the patients to eat food and therefore prolong life. Although the stent is also utilized for the treatment as described above, the general metallic stent is in adequate for reducing the restenosis. Since the stent could not prevent the restenosis efficiently and the cancer cell penetrates through the struts of the stent, the inner cavity of the esophagus gets narrowed. In order to solve such problems, thin cylindrical tube (sleeve-type) made of polyethylene and the like has been developed to surround the outside of the stent. But such a stent can not remedy the cancer sufficiently and fundamentally (U.S. Pat. No. 5,282,824).

As described above in the transluminal coronary angioplasty and the esophageal cancer treatment, the restenosis is reduced by physical inhibition of the stent implantation from vascular remodeling which contracts the blood vessel and the esophagus. At the restenosed sites, lesions of the blood vessel and the proliferation of the cancer cells also induces neointimal hyperplasia. In these cases, irradiation can prevent the cell proliferation and decrease the number of progenitor cells in the regenerating tissues.

Regarding the irradiation effects of inhibiting cell proliferation, ionizing radiation is reported to inhibit the thymidine uptake and the collagen synthesis in the cultured fibroblast and to prevent proliferative lesions or keloids generated after the surgical operation even at a low dosage. At that time, about 10 Gy (1000 rad) of fractionated irradiation may be delivered for the treatment, which does not affect the normal treatment process.

In order to effectively prevent the restenosis induced after operating the transluminal coronary angioplasty in coronary artery-stenosing diseases, the metallic stent coated with radionuclides such as Ir-192, Y-90, P-32 and the like has been utilized instead of the simple stent. Many researches on the radioactive stent have been made to prevent the restenosis fundamentally. Radiation emitted from the stents destructs the proliferating cells, and thus can be exploited to prevent the restenosis.

Hitherto, the radioactive metallic stent containing radioactive nuclides (Co-55, Co-56, Co-57, Mg-52, Fe-55) emitting gamma-ray and beta-ray has been prepared by Hehrlein et al. (Hehrlein, et al., Circulation, 88 suppl.I, 1993). The above stents were made of stainless steel (Palmaz-schatz, Johnson & Johnson International System) and bombed with protons in a cyclotron, which has been applied to rabbit iliac artery. At that time these radioactive nuclides of the stent have safety problems since the nuclides emitted gamma-rays and had a long half life. Thus pure beta-ray emitting nuclides such as P-32 has been adopted to develop the radioactive stent. Precisely, Strecker stent was reconstructed by the process which non-radioactive element P-31 was ion-implanted beneath the outer surface of the titanium wire. Resultantly the radioactive stent containing P-32 can be prepared by neutron irradiation in the nuclear reactor (Laird, J. R. et al., Circulation, 93: 529–536, 1996).

Besides, the methods for inserting the radioactive stent containing radioisotopes have been developed in order to perform the radiation therapy efficiently. The general stent is inadequate for the therapy since the radioactivity of the stent can not be controlled easily. The radioisotopes are mainly located on the surface of the coating material or in the metal alloy of the stent and the amount of the radioactivity emitted from the stent is mainly controlled by their half lives. Therefore after the insertion of the stent, the amount of the radioactivity can not be adjusted properly to the response of the patient's state. In order to settle the shortcomings, a minimally invasive medical device for providing the radiation treatment has been designed (U.S. Pat. No. 5,484,384).

Precisely, the medical device comprises an outer sheath, a wire coil and a flexible elongated member having distal and proximal portion which can slide through the sheath. The elongatable distal portion contains radioisotopes so that the device can be utilized for the radiation therapy controlling the radioactivity. And the distal portion forms a longitudinal curvature at the end of the wire coil and expands from the outer sheath so as to contact blood vessel. At that time the wire coil itself is composed of a radioactive metal alloy or is coated with radioisotopes such as Ir-192.

In addition, an invasive medical device which is combined with a sleeve containing radioisotopes dispersed onto the wire coil has been designed. In detail, the device comprises an elongatable distal portion, an expandable balloon and a catheter and can irradiate the wall of the blood vessel by expanding the wall of the balloon with radioactive liquid instead of gas (Fearnot, U.S. Pat. No. 5,484,384, 1996).

However, there are problems such as the inner cavity of the esophagus being narrowed again because tumor cells proliferates and cancer cells penetrates as shown in the previously developed stents. And the processes for coating and implanting the metallic stent is not simple. Therefore the stents have not been widely utilized clinically although many kinds of stents were developed.

Especially, radionuclides emitting beta-rays has such a short transmitting distance that it should be evenly dispersed throughout the surface of the metal wire for determining the absorption dose and the treatment dose of the radiation exactly. Besides, the space between the struts of the general stents can not be irradiated sufficiently in spite of uniform coating of the wires since most metallic stents have cylindrical shape composed of wires. It is also dangerous to use the stent since the contact region of the tissue with the metal struts may be irradiated too much.

Therefore, the present inventors have attempted to develop a radioactive stent resolving the above problems of the general metallic stent. Precisely the radioactive stent has been prepared by either covering the commercialized metallic stent with cylindrical thin sleeves made by mixing radionuclides with a carrier solution or by directly immersing the metallic stent in the above carrier solution and drying the solvents. Thus the radioactive stents prepared in the present invention were attempted to prevent the penetration of esophageal cancer cells and restenosing vascular diseases effectively.

SUMMARY OF THE INVENTION

The object of the present invention is to provide a radioactive stent for radiation therapy which is surrounded with a flexible sleeve containing radionuclides.

The present invention provides the radioactive stent which utilizes Sm-153, Dy-165, Ho-166, Er-169, P-32, Y-90, I-131, Re-186, Re-188, Pd-109 or Au-198 as beta-ray emitting nuclide and Ir-192, Co-57, Co-60, V-48 or I-125 as gamma-ray emitting nuclide.

The object of the present invention is to provide processes for preparing the radioactive stent.

The present invention provides a process for preparing the radioactive stent which comprises;

(S1) preparing a flexible sleeve by mixing radionuclide compound with a carrier and drying the mixture, (S2) surrounding a metallic stent with the above flexible sleeve, and (S3) adhering the flexible sleeve onto the above metallic stent.

The present invention also provides a process for preparing the radioactive stent which comprises;

(S11) inserting the metallic stent into a glass tube and immersing in a solution containing radionuclide compound, and (S12) maintaining the metallic stent in a horizontal position, rotating and drying.

Particularly, the radioactive stent of the present invention is prepared by utilizing a stable nuclide as the radionuclide of step (S1) and (S11) and irradiating the metallic stent obtained above with neutrons in a nuclear reactor or utilizing a radioactive compound as the radionuclide of step (S1) and (S11).

The present invention provides uses of the radioactive stent for preventing the restenosis of coronary artery and hepatobiliary duct cancer and for treating esophageal cancer and hepatobiliary cancer.

Figure 1:
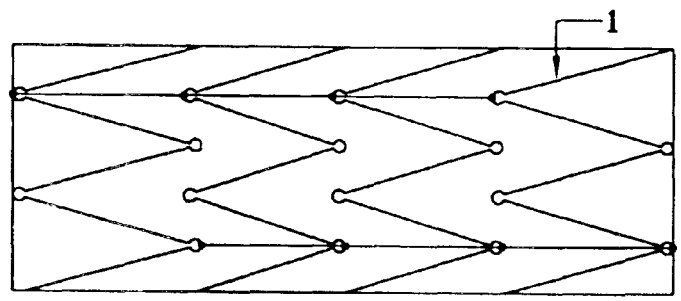
FIG. 1 depicts a side view of a commercialized general metallic stent.

1: strut (wire); 2: radionuclide; 3: polyurethane carrier; 4: epoxy adhesive agent; 5: metallic stent; 6: sheath; 7: radioactive sleeve; 8: stent introducer sheath; 9: introducer

DETAILED DESCRIPTION OF THE INVENTION

Referring to the drawings, the radioactive stent of the present invention will be described detaily as follows.

Figure 2:
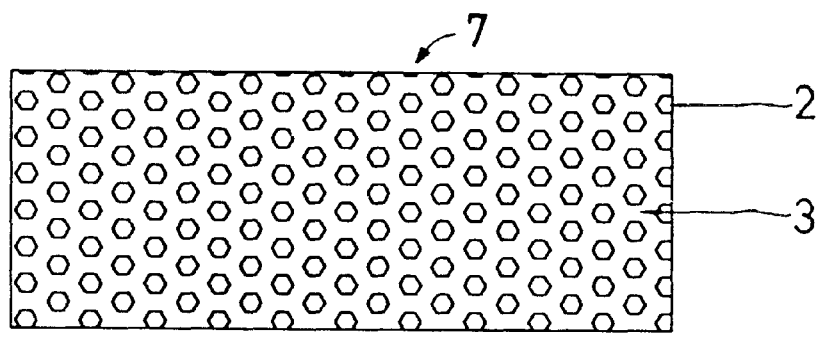
FIG. 2 depicts a side view of a radioactive sleeve which contains radionuclides evenly within a polyurethane carrier.
Figure 3:
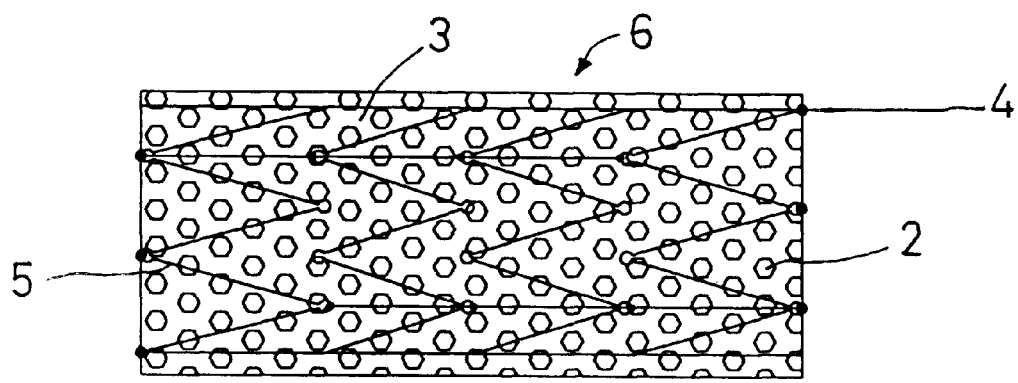
FIG. 3 depicts a side view of a radioactive stent in FIG. 1 surrounded with a cylindrical radioactive sleeve in FIG. 2.

The radioactive stent of the present invention is prepared by surrounding the metallic stent in FIG. 1 with a flexible cylindrical sleeve (6) of polyurethane carrier (3) containing radionuclides as depicted in FIG. 2 and FIG. 3 No. 6.

In this case, as radioactive nuclides (2), beta-ray emitting nuclides or gamma-ray emitting nuclides can be utilized. The stent (5) used in this invention can be made with metal such as stainless steel, titanium, nitinol, platinum and the like. The wires of the metallic stent (5) functioning as strut are surrounded with a sleeve (7) made of elastic expansible polymer or are treated with outer membrane, so that the gaps between the above wires are covered completely.

Practically, the sleeve (7) covering wires on the above stent (5) physically prevents cancer tissue or smooth muscle cell of coronary artery from invading. Gamma- or beta-rays and both the rays emitted from radionuclides (2) which are dispersed within the sleeve (7) disrupts cancer cell, smooth muscle cell and the like. Therefore the restenosis can be overcome fundamentally.

In this case, Sm-153, Dy-165, Ho-166, Er-169, P-32, Y-90, I-131, Re-186, Re-188, Pd-109 or Au-198 are utilized as beta-ray emitting nuclide. Ir-192, Co-57, Co-60, V-48 or I-125 are utilized as gamma-ray emitting nuclide and Pd-103 as both gamma- and beta-ray emitting nuclide. In addition most radionuclides used for the general therapeutic treatment can be exploited in preparing the above radioactive stent of the present invention.

The radioactive stent (6) of the present invention can be utilized widely and extensively for preventing restenosis related with diseases in coronary artery, hepatobiliary duct, esophagus and the like and for inhibiting cell proliferation. The radioactive stent can be prepared variously according to size and shape.

Particularly, the radioactive polymer used in the radioactive stent of the present invention can be provided as a balloon-type polymer as well as a sleeve-type. In this case, the balloon-type radioactive polymer can be exploited directly on the instrument for the angioplasty or after adhering onto a balloon-type stent. This balloon-type radioactive stent is depicted in FOGS. 5a and 5b.

The processes for preparing the radioactive stent (6) of the present invention will be described detaily as follows.

The radioactive stent (6) is prepared by the 3-step process which comprises;

(S1) preparing a flexible sleeve (7) by mixing radionuclide compound (2) with a carrier (3) and drying the mixture, (S2) surrounding a non-radioactive metallic stent with the above flexible sleeve (7) exteriorly, and (S3) adhering the flexible sleeve onto the above metallic stent (5).

Detaily in the step (S1) preparing a radioactive sleeve by mixing radionuclide compound (2) with a carrier (3), the radioactive compound and carrier material (3) are dissolved in the mixed solvent of dimethlyformamide (DMF) and tetrahydrofurane (THF) and poured into a glass tube. Maintaining the metallic stent in a horizontal position, the solvent is evaporated so that a radioactive sleeve can be prepared. And then the above radioactive sleeve is separated carefully from the inner wall of the glass tube so as to produce a radioactive sleeve (7).

Figure 4A:
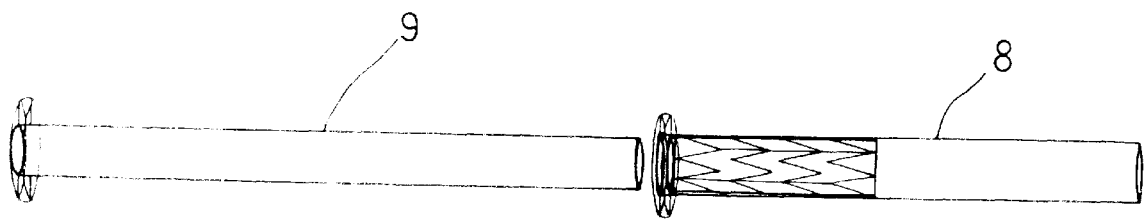
FIG. 4a depicts a compressed state of the radioactive stent within a cylindrical sheath.
Figure 4B:
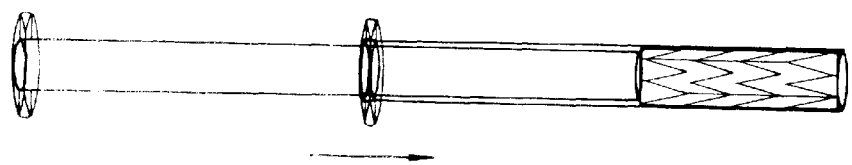
FIG. 4b depicts the stent pushed by an introducer to the state right before expanding the sleeve and FIG. 4c, an expanding state which the stent is expanded into full size at a determined position.
Figure 4C:
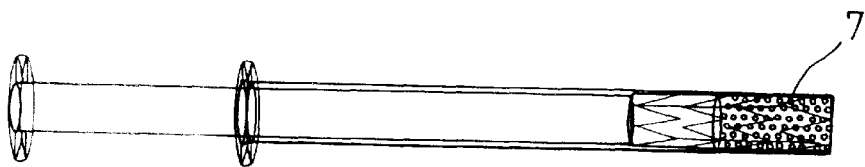
FIG. 4 depicts stages respectively which the radioactive stent in FIG. 1 is inserted into the cylindrical radioactive sleeve in FIG. 2 as described in FIG. 3.
Figure 5A:
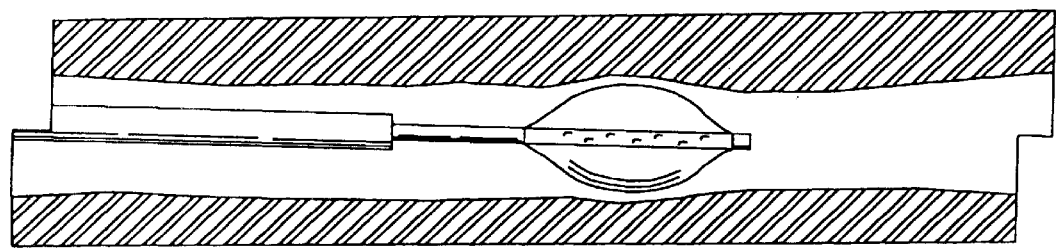
FIG. 5a depicts a compressed state in a lesion site and FIG. 5b, an expanding state into full size.
Figure 5B:
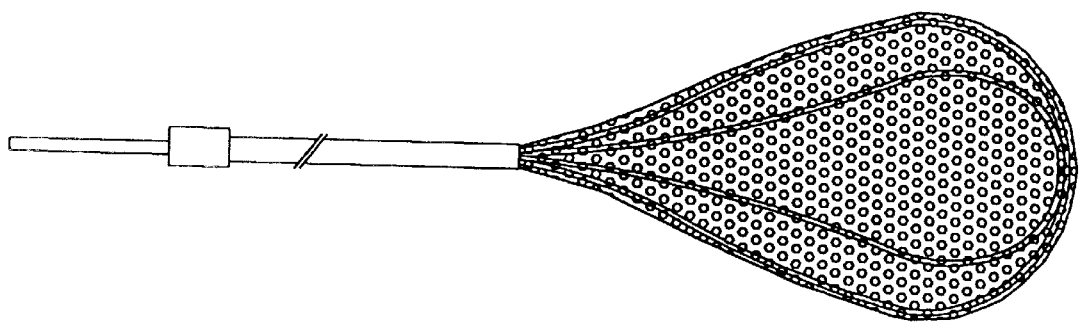
FIG. 5 depicts a balloon-type radioactive stent surrounded by the radioactive sleeve respectively.

Then in the step (S2) described in FIG. 4a–4c, the radioactive stent (5) is inserted into the radioactive sleeve (7) produced in the step (S1). Particularly as shown in FIG. 4a, the metallic stent (Cook-Z stent) is inserted into a cylindrical stent introducer sheath (8). Then as shown in FIG. 4b, the metallic stent (5) is intruded into the sheath (8) by using an introducer (9) and as shown in FIG. 4c the radioactive sleeve (7) expands at the determined position, and surrounds the metallic stent.

Finally in the step (S3) described in FIG. 3, the sleeve (7) is adhered onto the stent (5) by adding an adhesive agent such as epoxy on the right and left edges of the inner wall in the sleeve (7) and on the right and left edge of the outer wall in the metallic stent (5) respectively.

At that time, for a radioactive compound contained within the sleeve (7), both stable nuclides and radioactive nuclides can be utilized as radionuclide. As irradiation method preparing the radioactive stent of the present invention, both pre-irradiation method and post-irradiation method can be adopted.

First, in order to prepare the radioactive stent by using the pre-irradiation method, the radionuclide (2) used in the above step (S1) should be radioactive.

The radionuclide (2) is evenly mixed with the above carrier material evenly and dried to be dispersed and fixed within the carrier polymer (3) so that radioactive material is not released exteriorly. When preparing the radioactive stent by using the above pre-irradiation method, operators should be cautious to minimize damages by bombing.

On the other hand, in order to overcome the above shortcoming, the post-irradiation method can be adopted. The method comprises; adhering the sleeve which contains stable isotopes onto a non-radioactive stent and then irradiating it with neutrons in a nuclear reactor. Preferably, stable nuclide should be used as a radioactive source in the step (S1-1). Metal elements composing the metallic stent (5) should not become radioactive easily by bombing with neutrons and after completing the step (S1), the non-radioactive sleeve should be bombed with neutrons in a nuclear reactor additionally (S1-1).

In the above process, Ho-165, Dy-164, Y-89, P-31 and Ir-191 compound are preferably utilized as stable nuclide (3). Polyurethane, latex, butyl rubber, acryl type, chloroprene type, PVA type or nylon type polymer are appropriate to be utilized as a carrier material. And preferably the thickness of the flexible sleeve is 40–100 µm. In addition, acryl series, chloroprene series, PVA series, nylon series and the like can be utilized as carrier material.

But in the post-irradiation method, the metallic stent itself may emit radioactive rays due to neutron bombing. Therefore preferably metal element which does not become radioactive easily such as platinum, titanium, nitinol etc. is utilized rather than stainless steel. And as a stable nuclide contained in the sleeve, element having a larger neutron absorption cross-section is preferred such as Sm-152, Dy-164 and Ho-165 which becomes radioactive easily and produces many radioactive nuclides like Sm-153, Dy-165 and Ho-166.

Particularly, in order to analyze neutron activation of the metallic stent, the commercialized metallic stent is irradiated with neutrons and then the radionuclides which were produced have been analyzed by using a multichannel analyzer. As a result, it is identified that stainless steel can not be used appropriately for the metallic stent of the present invention since it is activated much by neutron bombing.

In addition, the radioactive stent of the present invention is prepared by immersing a metallic stent directly into the above carrier solution and drying for attaching radioactive compound onto the stent (5).

Particularly, the radioactive stent is prepared by the process which comprises;

(S11) inserting the metallic stent (5) into a glass tube and immersing it in a solution containing radionuclide compound, (S12) maintaining the metallic stent (5) in a horizontal position and drying it, (S13) separating the above stent (5) from the glass tube carefully.

The above process can also be performed by using both the pre-irradiation method and the post-irradiation method.

The above metallic stent inserted into the glass tube is spun and dried, if necessary heated. This makes the metallic stent and radioactive sleeve adhere strongly and therefore an additional adhesive agent for preventing separation is not needed.

And all kinds of radioactive stent surrounded with the radioactive sleeve of the present invention can be belonged to the scope of the present invention.

Figure 6A:
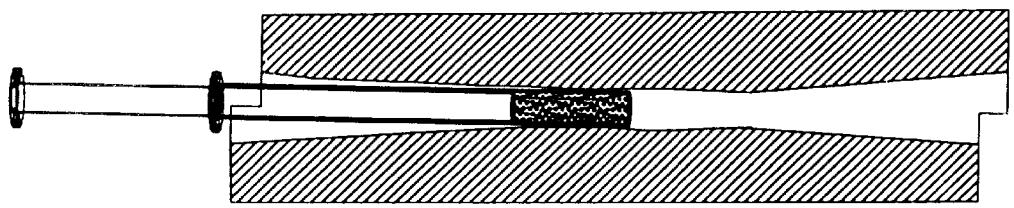
FIG. 6a depicts a compressed state right before expanding from the introducer to the lesion site, FIG. 6b, an expanding state during the insertion and FIG. 6c, an expanded state.
Figure 6B:
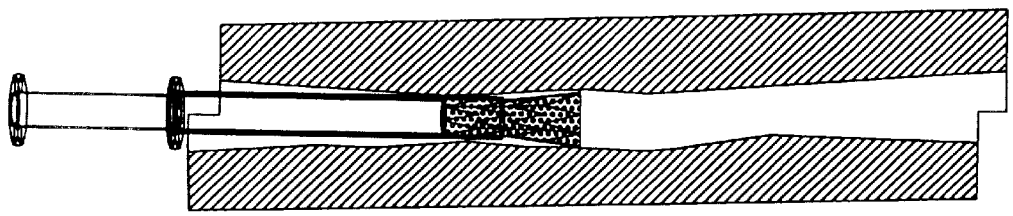
FIG. 6 depicts stages which the radioactive stent in FIG. 3 is inserted at the lesion site, schematically and respectively.
Figure 6C:
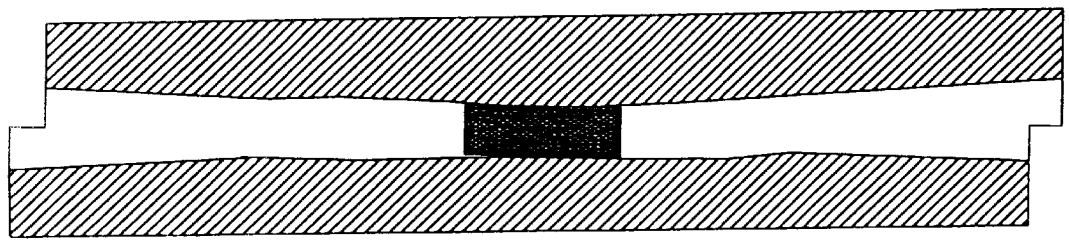

The process for inserting the radioactive stent (6) in FIG. 3 onto the lesion site such as esophagus is described schematically in FIG. 6. The radioactive stent (6) can be inserted into human body by performing the same method of the general stent. First as shown in FIG. 6a, the introducer which has fixed the radioactive stent of compressed state is inserted to the lesion sites for the treatment. And then as shown in FIG. 6b, the introducer is intruded into the sheath, expanding the radioactive stent. Finally, the radioactive stent is fixed to the lesion site and supports it after the introducer and the sheath is drawn out.

Practical and presently preferred embodiment of the present invention are illustrated as shown in the following Examples.

However, it will be appreciated that those skilled in the art, on consideration of this disclosure, may make modification and improvements within the spirit and scope of the present invention.

EXAMPLES

Example 1

The preparation of the radioactive sleeve containing Ho-165 (flexible sleeve, $^{165}$Ho-FS) by using the post-irradiation method.

(1-1) The utilization of polyurethane (PU) as carrier material

In order to prepare the sleeve containing radionuclides, 2.4 g of Ho(NO$_3$)$_3$.5 H$_2$O and 2,4 g of polyurethane (PU) were dissolved completely in co-solvent 4 ml of dimethlyformamide (DMF) and 40 ml of tetrahydrofurane(THF) at room temperature.

A cylinder-type glass tube of 1 cm in diameter and 10 cm in length was laid on a support and was adjusted horizontally, and then both ends of the glass tube were fixed on a rotary device.

2 ml of above solution containing PU was drawn with syringe and was added into the glass tube. Then while the glass tube was rotated in a constant velocity, the solvent was volatilized. THF solvent was evaporated first since it was highly volatile. After 3 hours the PU sleeve was formed within the above glass tube, separated carefully from the inner wall of the tube by using a thin stainless steel bar, then washed with D.W. several times and dried.

Figure 7:
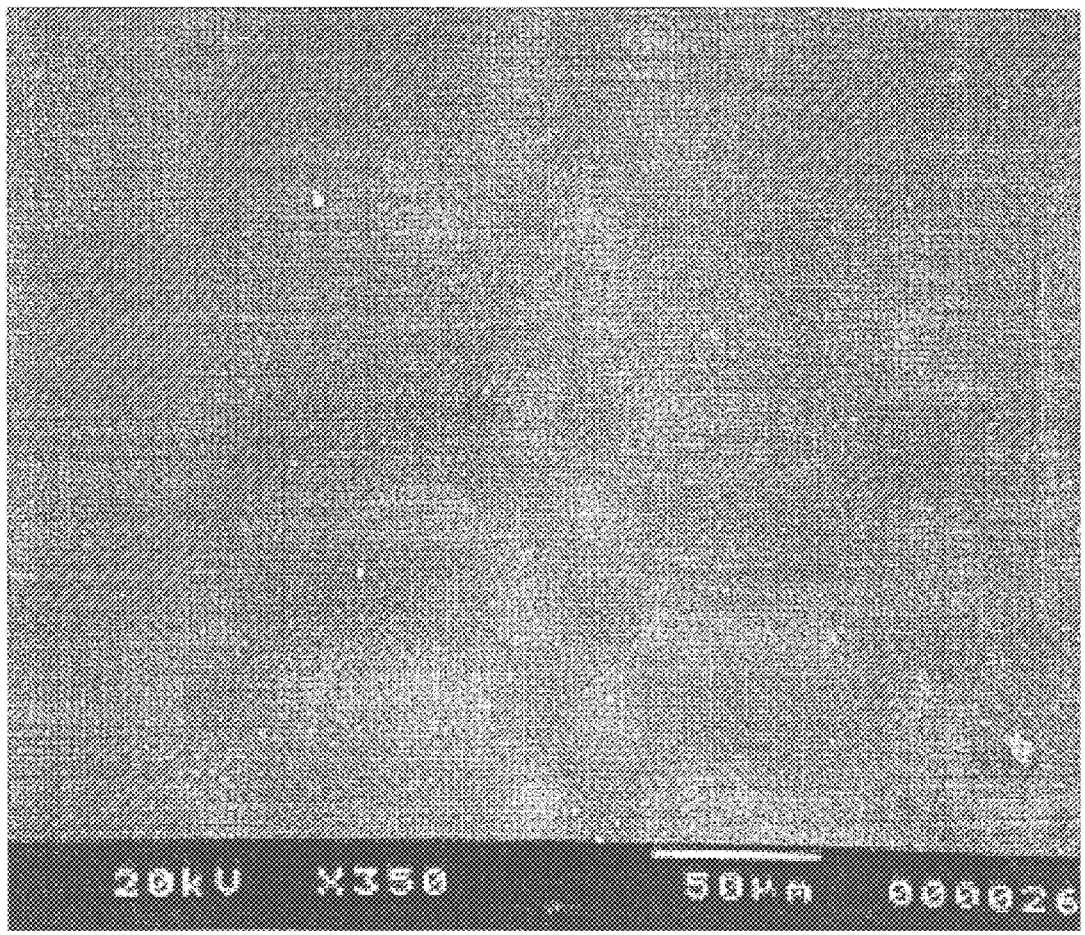
FIG. 7 depicts a polyurethane carrier containing radionuclides, Ho-166 by performing scanning electron microscopy (SEM, X 500)
Figure 8:
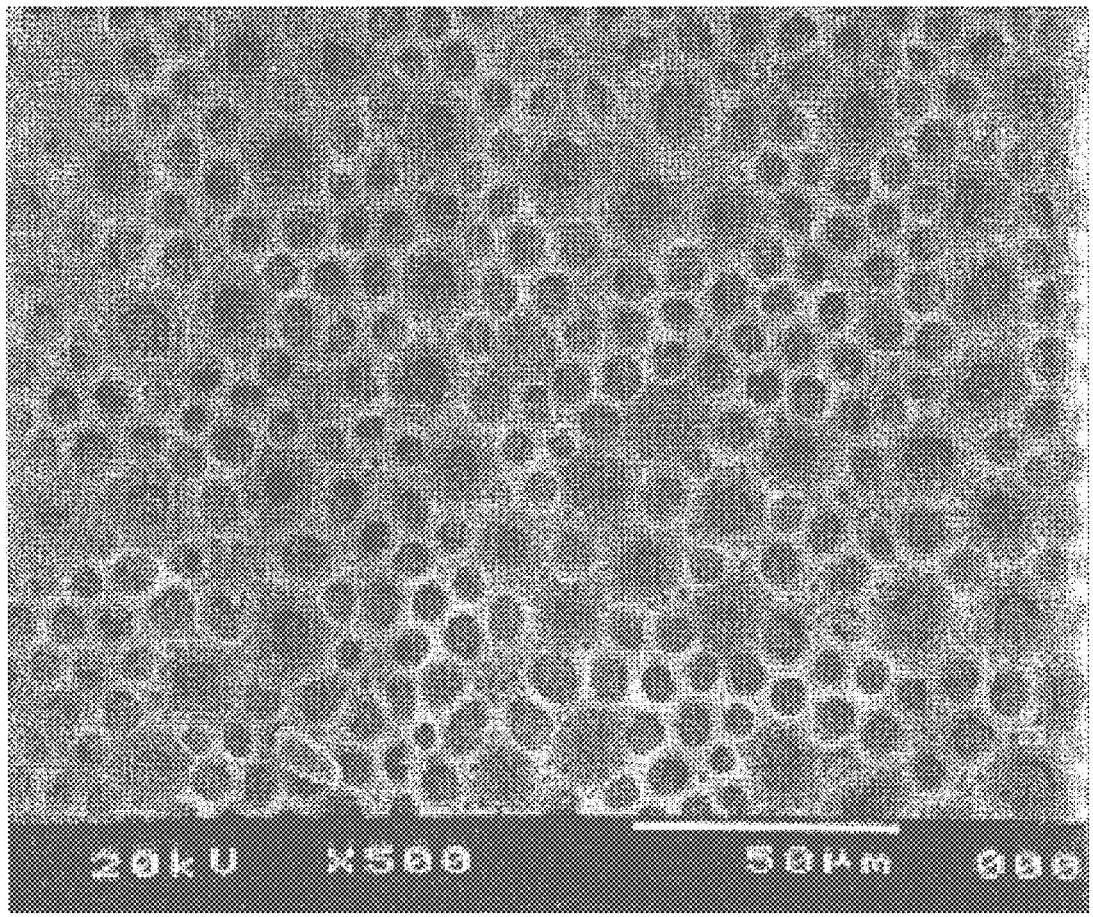
FIG. 8 depicts a polyurethane carrier without radionuclide by performing scanning electron microscopy (SEM, X 500)
Figure 9:
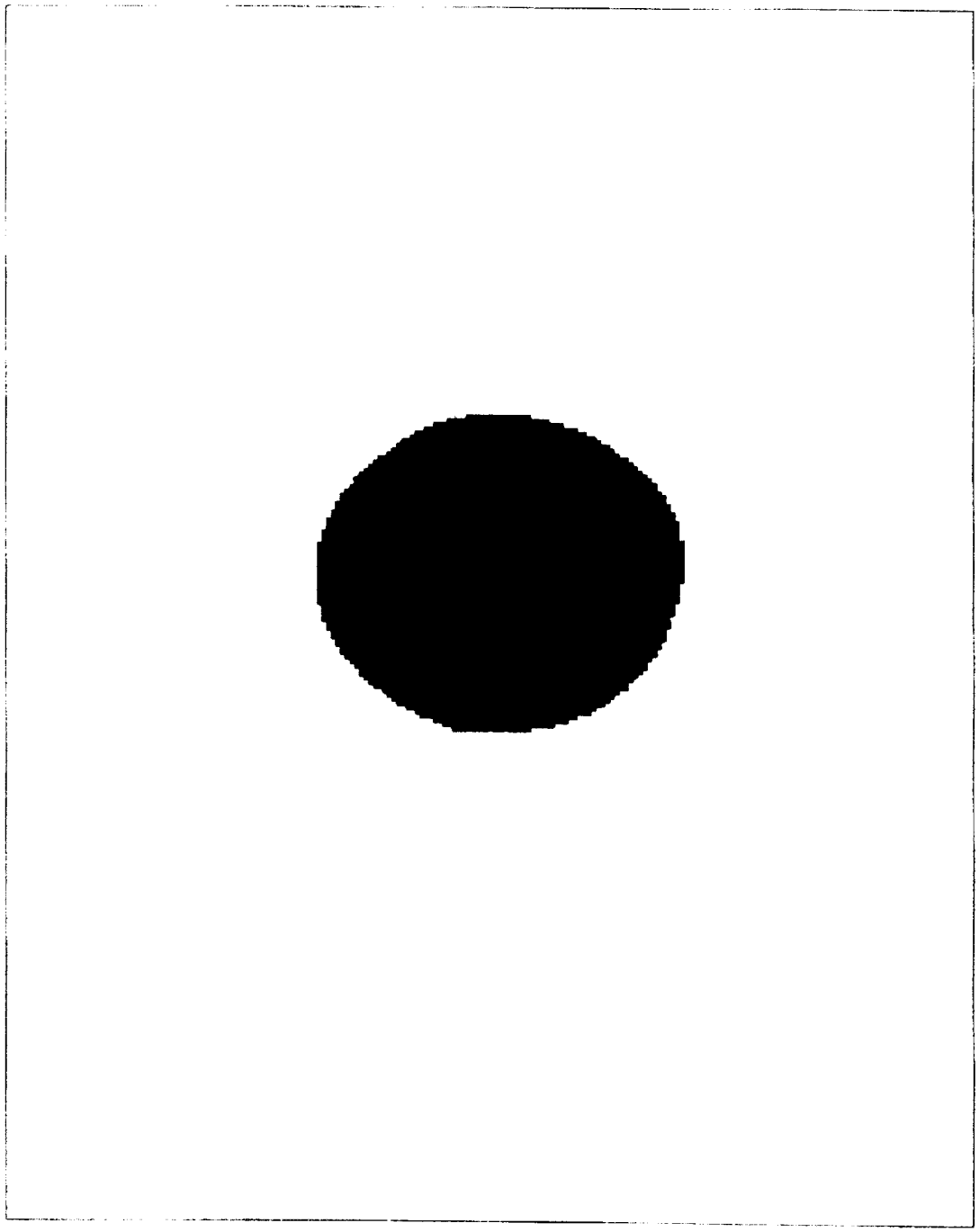
FIG. 9 depicts the radioactive sleeve which contains radionuclide, Ho-166 and is cut in a circle form by performing autoradiography.

In order that the sleeve prepared above be converted to the radioactive sleeve, the sleeve $^{165}$Ho-FS was cut to have 3 cm in length and then irradiated with neutrons in the nuclear reactor (neutron flux: $1.25 \times 10^{13}$n/cm$^2$sec, power: 15 MW, HANARO). As a result, the radioactive sleeve $^{166}$Ho-FS was obtained and the polyurethane sleeves with radionuclides and those without radionuclides were observed respectively by performing scanning electron microscopy shown in FIG. 7 and 8. And the sleeve shown in FIG. 7 was also observed by performing autoradiography.

(1-2) The utilization of latex as carrier material

By the same procedure of the step (1-1), $^{165}$Ho(NO$_3$)$_3$.5 H$_2$O is well mixed with the mixed solvent of DMF and THF and sulfur was added into latex solution and mixed evenly.

A mold was immersed in this solution and taken out. The mold was spun regularly preventing the solution from flowing to one side, and dried and then vulcanized by heating. The sleeve was separated from the mold carefully.

(1-3) The utilization of butyl rubber (isobutyleneisoprene rubber) as carrier material By the same procedure of the step (1-1), $^{165}$Ho(NO$_3$)$_3$.5 H$_2$O is well mixed with the mixed solvent of DMF and THF and sulfur was added into butyl rubber solution which has elastic and flexible property and mixed evenly.

A mold was immersed in this solution and taken out. The mold was spun regularly preventing the solution from flowing to one side, and dried and then vulcanized by heating. The sleeve was separated from the mold carefully.

Example 2

The preparation of the radioactive sleeve containing Ho-166 by using the pre-irradiation method.

(2-1) The utilization of polyurethane(PU) as carrier material

Foremost $^{165}$Ho(NO$_3$)$_3$.5 H$_2$O was irradiated with neutrons in the nuclear reactor and converted to $^{166}$Ho(NO$_3$)$_3$.5 H$_2$O.

According to the same process of Example 1, 2.4 g of $^{166}$Ho(NO$_3$)$_3$.5 H$_2$O and 2.4 g of PU were dissolved completely in mixed solvent of 4 ml of DMF and 40 ml of THF at room temperature.

A cylinder-type glass tube of 1 cm in diameter and 10 cm in length was laid on a support and was adjusted horizontally, and then both ends of the glass tube were fixed on a rotary device.

2 ml of the above solution containing PU was drawn with syringe and was added into the glass tube. Then while the glass tube was rotating in a constant velocity, the solvent was volatilized. After 3 hours the PU sleeve was formed within the above glass tube, separated carefully from the inner wall of the tube by using a thin stainless steel bar, then washed with D.W. several times and dried.

(2-2) The utilization of latex as carrier material

By performing the same procedure of the step (2-1), $^{165}$Ho(NO$_3$)$_3$.5 H$_2$O was irradiated with neutrons in the nuclear reactor and converted to $^{166}$Ho(NO$_3$)$_3$.5 H$_2$O. Sulfur and the mixed solvent of DMF and THF containing the above radionuclide in aqueous solution was added into latex solution and well mixed.

A mold was immersed in this solution and taken out. The mold was spun regularly preventing the solution from flowing to one side, and dried and then vulcanized by heating. The sleeve was separated from the mold carefully.

(2-3) The utilization of butyl rubber (isobutyleneisoprene rubber) as carrier material By performing the same procedure of the step (2-1), $^{165}$Ho(NO$_3$)$_3$.5 H$_2$O was irradiated with neutrons in the nuclear reactor and converted to $^{166}$Ho(NO$_3$)$_3$.5 H$_2$O. Sulfur and the mixed solvent of DMF and THF containing above radionuclide was added into butyl rubber solution which has elastic and flexible property and well mixed.

A mold was immersed in this solution and taken out. The mold was spun regularly preventing the solution from flowing to one side, and dried and then vulcanized by heating. The sleeve was separated from the mold carefully.

As radioisotope of the above process, all the curative radionuclides such as I-131, I-125, Au-198, Ir-192, Co-60, Yb-169, Pd-103, Pd-109, Sm-153, Dy-165, Er-169, P-32, Y-90, Re-186, Re-188 in addition to Ho-166 can be utilized.

Example 3

The preparation of the radioactive stent assembly ($^{166}$Ho-SA)

(3-1) The preparation of the radioactive stent assembly I

Figure 10:
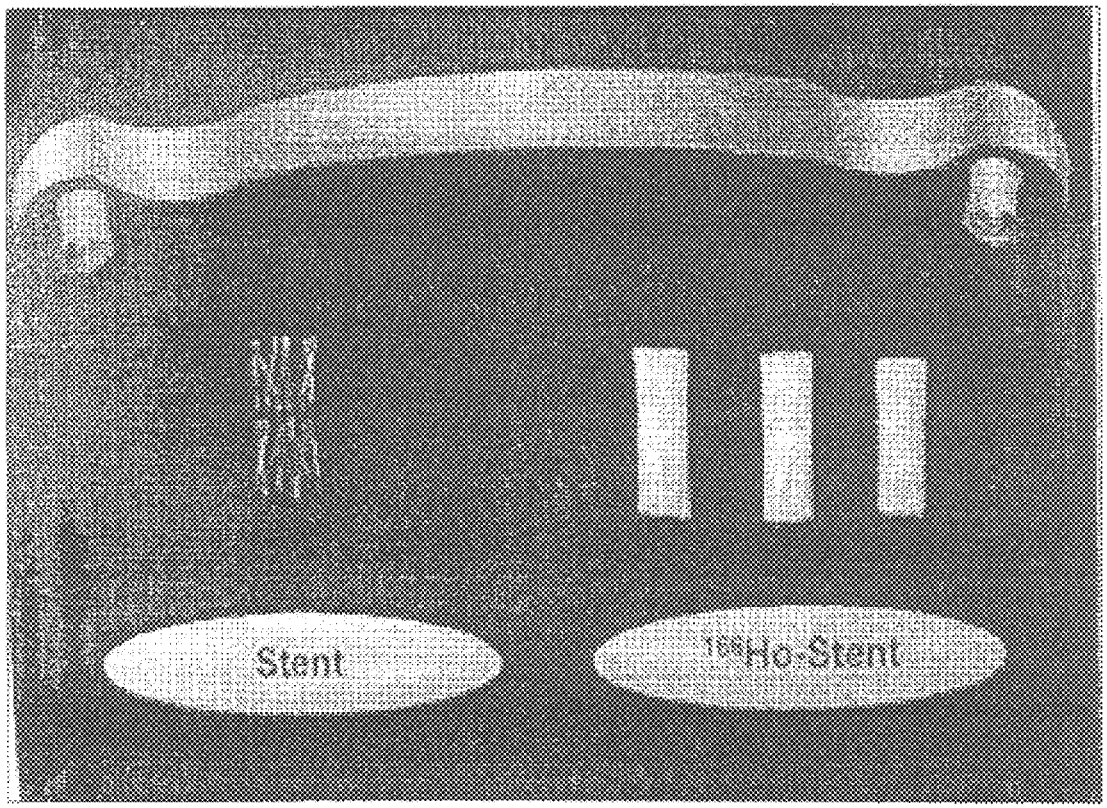
FIG. 10 depicts a radioactive stent which is made of stainless steel and is surrounded with the radioactive sleeve containing radionuclides, Ho-166 by performing autoradiography; in the upper part, a radioactive band of sleeve before manipulation, in the middle part, a general stent made of stainless steel and in the right part the radioactive stent.

A radioactive stent assembly was prepared by inserting the metallic stent(Cook-Z stent) established 10 previously into the inner wall of the stent introducer sheath. In detail, after the sheath (8) was pushed into $^{166}$Ho-FS, a pushing bar was fixed in the stent introducer sheath (9). Then the sheath was withdrawn slowly so that the metallic stent was expanded and stuck to the inner wall of the sleeve and $^{166}$Ho-FS was disposed to surround the outer metallic stent. The radioactive stent made of stainless steel and covered with the radioactive sleeve was observed by performing autoradiography shown in FIG. 10.

(3-2) The preparation of the radioactive stent assembly II

By performing the same process for preparing $^{165}$Ho-FS as Example 1, non-radioactive stent assembly was manufactured. Detaily a metallic stent was set into the glass tube, immersed in PU solution Ho-165 compound, spun maintaining a horizontal position, dried and separated from the above glass tube according to the same procedure of the step (3-1). And then the stent assembly was irradiated with neutrons in the nuclear reactor so as to obtain the radioactive stent assembly.

Example 4

Neutron activation analysis of the metallic stent

In order to overcome the problem of the post-irradiation method, the commercialized metallic stents which are made of stainless steel, titanium, nitinol or platinum were cut and irradiated with neutrons for a determined period, using PTS (Pheumatic Transfer System) device. And then the kind of radionuclides which were produced were analyzed by using a multichannel analyzer. As a result, it is identified that the stent made of stainless steel can not be used appropriately for preparing the radioactive stent by using the post-irradiation method since it contains radionuclide much.

As described above, the radioactive stent of the present invention is surrounded with the outer sleeve made of flexible material and is made radioactive by bombing the sleeve containing radionuclides. And this enables smooth muscle cell to be destructed effectively comparing with the general stent using non-radioactive sleeve. Therefore this radioactive stent prevents restenosis induced by cell proliferation of the lesion site and penetration in esophageal cancer, etc. efficiently.

Comparing with the general stent which is coated with radioactive material on the outer surface of wires or which contains radioisotopes within the metal alloy, the sleeve of the radioactive stent of the present invention surrounding the outer wall which contains radionuclides evenly is irradiated wholly. Thus the radioactive stent of the present invention can be produced without complex coating steps and facilitate implanting process. Regardless of transmitting distance of irradiation in each radionuclide, lesion site can be uniformly irradiated so as to evenly destruct the cells. Therefore the distance from the metallic wires does not affect radiation dosage and does not provoke deviation of the dosage. According to the irradiation method, almost all kinds of radionuclides can be utilized and so the scope of the usable stent is wide regardless of radionuclide kinds.

Therefore the radioactive stent of the present invention can maximize the therapeutic effects in occluded diseases such as arteriosclerosis, hepatobiliary duct cancer and esophageal cancer. The effects are maximized since the lesion sites are irradiated evenly and closely and this enables the prevention of the restenosis of coronary artery and the penetration of cancer cells into lumen.

What is claimed is:

1. The combination of a radioactive stent for radiation therapy and flexible sleeve said radioactive stent surrounded with said flexile sleeve containing radionuclides, wherein said stent is constituted by an expansible framework structure to expand in sleeve-type or balloon-type fashion.

2. The combination according to claim 1, wherein the radionuclide contains Sm-153, Dy-165, Ho-166, Er-169, P-32, Y-90, I-131, Re-186, Re-188, Pd-109 or Au-198 as beta-ray emitting nuclide and contains Ir-192, Co-57, Co-60, V-48 or I-125 as gamma-ray emitting nuclide.

3. The combination according to claim 1, wherein the flexible sleeve is constituted by a dried mixture of said radionuclides with carrier material.

4. The combination according to claim 3, wherein the carrier material contains polyurethane, latex, or butyl rubber.

5. The combination according to claim 3, wherein the flexible sleeve is 40–100 $\mu$m in thickness.

6. The combination of claim 1, wherein said stent is constituted by a wire strut structured and arranged to expand in cylindrical or sleeve-type fashion.

7. The combination of claim 1, wherein said stent is constituted by a wire framework structured and arranged to expand in balloon-type fashion.

8. Use of the combination of claim 1 for preventing restenosis of coronary artery, hepatobiliary duct and for treating esophageal cancer and hepatobiliary duct cancer.

* * * * *